United States Patent [19]
Yokomori et al.

[11] Patent Number: 5,233,668
[45] Date of Patent: Aug. 3, 1993

[54] METHOD AND APPARATUS FOR DISCRIMINATING AGGREGATION PATTERN

[75] Inventors: Yasuhiko Yokomori; Toshiyuki Furuta, both of Yokohama; Naoki Ozawa; Masato Ohta, both of Kawasaki; Hideo Suda, Yokohama; Shogo Kida, Kawasaki; Ryohei Matsumoto, Yokohama; Kunio Kurata; Yoshinobu Kubo, both of Matsudo; Yoshiharu Matsuoka, Kamagaya; Masahiro Kato, Tokyo, all of Japan

[73] Assignees: Suzuki Motor Corporation, Shizuoka; Dainabot Co., Ltd., Tokyo, both of Japan

[21] Appl. No.: 700,568

[22] Filed: May 15, 1991

[30] Foreign Application Priority Data
May 25, 1990 [JP] Japan .................................. 2-136019

[51] Int. Cl.$^5$ ........................ G06K 9/00; G01N 21/59
[52] U.S. Cl. ............................................. 382/6; 382/53
[58] Field of Search ........................................ 382/6, 53

[56] References Cited
U.S. PATENT DOCUMENTS

| | | | |
|---|---|---|---|
| 4,702,595 | 10/1987 | Mutschler et al. | 382/6 |
| 4,709,274 | 11/1987 | Tanioka | 382/53 |
| 4,856,073 | 8/1989 | Farber et al. | 382/6 |
| 4,887,305 | 12/1989 | Shimura | 382/6 |
| 5,068,909 | 11/1991 | Rutherford et al. | 382/53 |
| 5,072,382 | 12/1991 | Kamentsky | 382/6 |

Primary Examiner—David K. Moore
Assistant Examiner—Barry Stellrecht
Attorney, Agent, or Firm—Flynn, Thiel, Boutell & Tanis

[57] ABSTRACT

A method and apparatus for discriminating aggregation patterns includes detection of an image of the aggregation pattern and dividing the image into a plurality of image line data using a photoelectric element. The image line data defines an image waveform and includes a maximum image value. High and low image levels are defined based on the maximum image value. These high and low image levels are used to determine first and second areas of the aggregation pattern image, which first and second areas respectively include image values at least as large as the high and low image levels. An area difference between the first and second areas and a level difference between the high and low image levels are then calculated, along with a ratio of the area difference to the level difference. The calculated area difference and ratio are then compared with a predetermined reference value to discriminate whether or not the aggregation pattern is positive.

5 Claims, 5 Drawing Sheets

[NON-AGGREGATION
(NEGATIVE)]

[AGGREGATION
(POSITIVE)]

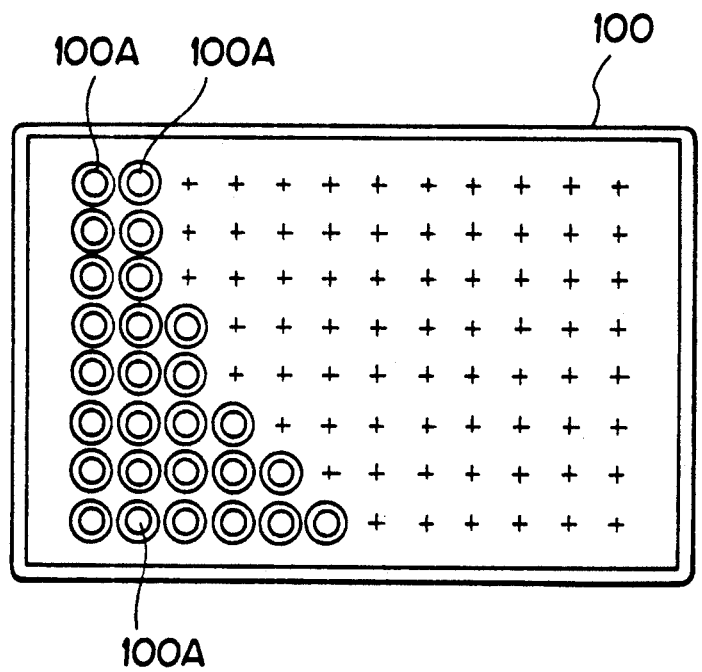

METHOD AND APPARATUS FOR DISCRIMINATING AGGREGATION PATTERN

CROSS REFERENCE TO RELATED APPLICATION

This application is related to copending U.S. Ser. No. 07/520,093 filed on May 7, 1990, now U.S. Pat. No. 5,096,835 and assigned to the assignees of the present invention.

1. Field of the Invention

The present invention relates to a method and apparatus for processing data to discriminate an aggregation pattern and, more particularly, to a method and apparatus which are suitable to discriminate an aggregation pattern of blood particles by the microtiter method which is used to discriminate a blood type or to detect an antigen and an antibody.

2. Background of the Invention

In the medical field, hitherto, there has widely been used a method whereby aggregation patterns of blood particles, latex particles, carbon particles, and the like are discriminated and various components (for instance, blood type and various antibodies, or various proteins, etc.) in the blood, viruses, and the like are detected and analyzed. As a method of discriminating the aggregation patterns, the microtiter method is relatively frequently used.

In the discrimination of the aggregation pattern, the presence or absence of an aggregation is synthetically judged in a manner such that a distribution of the particles in a well (reactive vessel) is detected as an area of the portions whose luminances are equal to or less than a predetermined luminance or compared with a reference pattern or a reference non-aggregation pattern and, further, a continuous stage dilution series of a specimen sample is formed, or the like. For instance, a shadow of FIG. 5(a) is determined to be negative and a shadow of FIG. 5(b) is decided to be positive.

FIG. 6 shows a conventional example wherein an aggregation pattern P in a well (i.e. reactive vessel) 100A formed on a microplate 100 is optically projected onto a CCD line sensor 101. The line sensor 101 or microplate 100 is relatively sequentially finely moved in the direction perpendicular to the paper surface, thereby obtaining a two-dimensional (light/dark) image of the aggregation pattern P. In FIG. 6, reference numeral 102 denotes a light source, 103 indicates an image forming lens, and 104 a lens holder.

The microplate 100 having a plurality of concave reactive vessel (well) sections 100A is actually used as shown in FIG. 7. For instance, either a positive or negative aggregation pattern as shown in FIG. 5 is produced in each well by the antigen antibody reaction between the component in the blood and a reagent.

In the above conventional example, in many cases, the positive/negative discrimination is executed by the operator by visually observing a cross sectional waveform of the peak value. Or, on the basis of a threshold value of a predetermined level, an area at the threshold value level is obtained and the presence or absence of the positivity is discriminated based on the magnitude of the area.

However, in the discrimination depending on such an area, for instance, in the case of the line data of the waveforms shown in FIGS. 4(a)–4(c), the areas associated with FIGS. 4(a) and 4(b) are the same, so that the waveform of FIG. 4(b), which should inherently be "positive", is often erroneously determined to be "negative". Each hatched area shown in FIG. 4 represents the portion of the aggregation image having image levels at least as large as the specified threshold value.

It is an object of the invention to improve upon the conventional example and, particularly, to provide a method and apparatus for discriminating an aggregation pattern in which an aggregation pattern which should inherently be "positive" can be determined to be "positive".

According to the invention, one aggregation pattern is detected and dissolved (i.e. partitioned or divided) into a plurality of line data by using a photoelectric element. For a detection waveform of the line data including a maximum value of the plurality of line data, two high and low cutting levels corresponding to the maximum value of such a waveform are set. A difference between areas at two high and low positions of the aggregation pattern which is cut by those two cutting levels is obtained and is set as a first characteristic value. A level difference between the two cutting levels is calculated, and a ratio of the area difference to the level difference is calculated and is set as a second characteristic value. The first and second characteristic values are then compared with a predetermined reference value, thereby discriminating whether the aggregation pattern is positive or not. Due to the above construction, the above object is accomplished.

BRIEF DESCRIPTION OF THE DRAWINGS

An embodiment of the invention will be described hereinbelow on the basis of the drawings, wherein:

FIG. 7 is a plan view showing an example of a conventional microplate having a plurality of reactive vessels.

DETAILED DESCRIPTION

Figure 1:
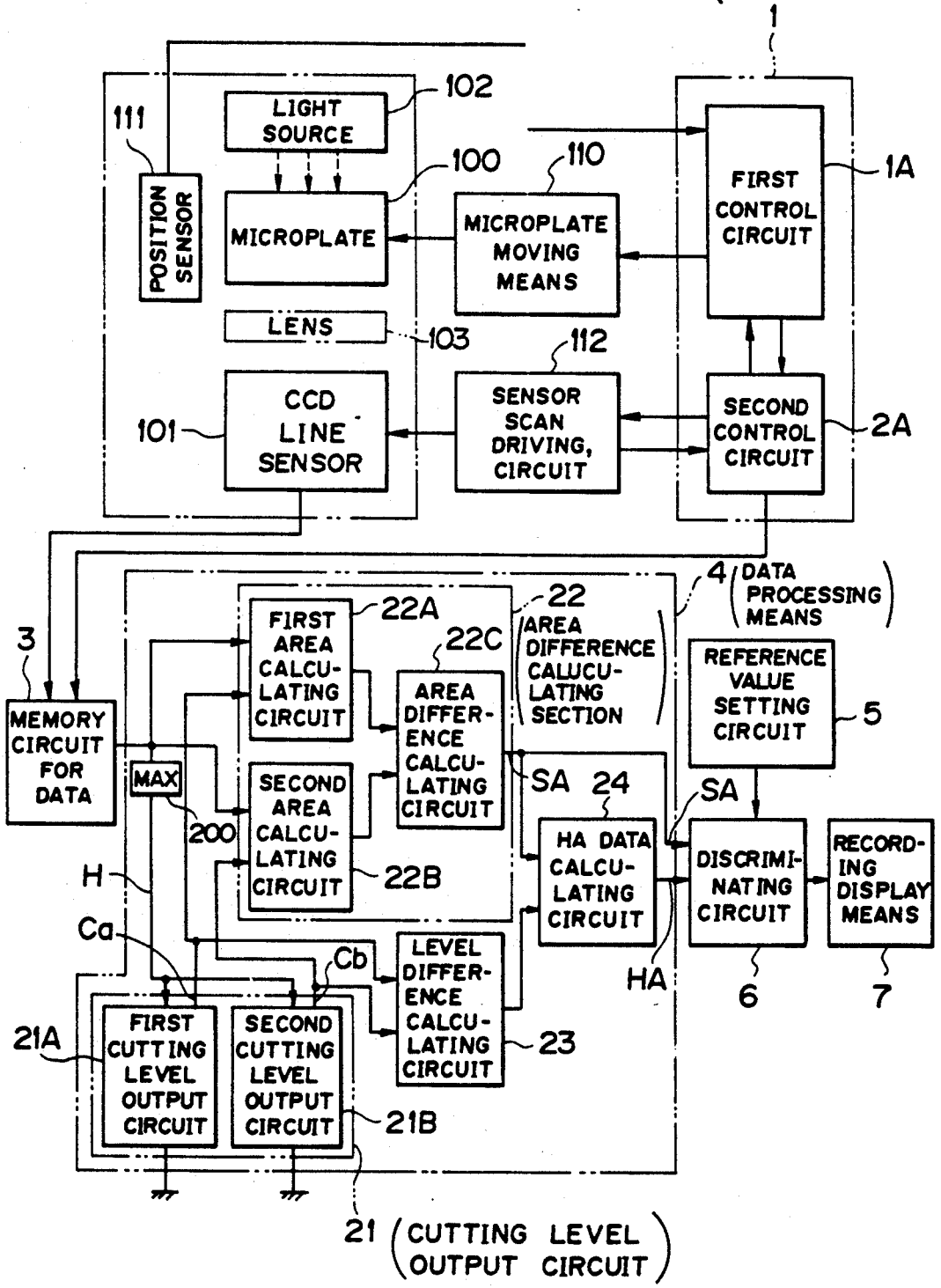
FIG. 1 is a block diagram showing an embodiment of the invention.
Figure 6:
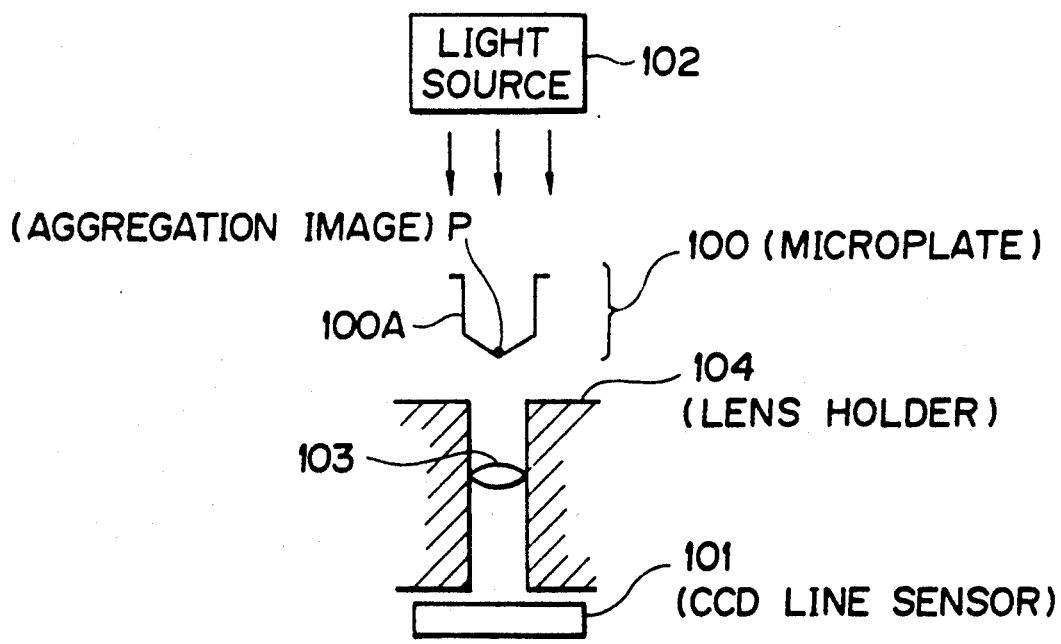
FIG. 6 is an explanatory diagram showing a conventional arrangement of a reactive vessel, an optical system and a CCD line sensor used to obtain an aggregation pattern.

In FIG. 1, the CCD line sensor 101 is arranged below the microplate 100 having a reactive vessel through an optical system 103 in a manner similar to the foregoing conventional example shown in FIG. 6. The microplate 100 is driven by microplate moving means 110 and sequentially moved relative to the CCD line sensor 101 by a micro distance at a time in a first direction perpendicular to the scanning direction of the CCD line sensor 101, and in a second direction opposite to the first direction. Reference numeral 111 denotes a position detecting sensor. The position detecting sensor 111 is used to determine a reciprocation moving distance of the microplate 100. An output of the sensor 111 is sent to a first control circuit IA in a main control section 1. Due to this, the position of the microplate 100 is always specified and the microplate 100 is moved forward, backward, or stopped as necessary.

Figure 2:
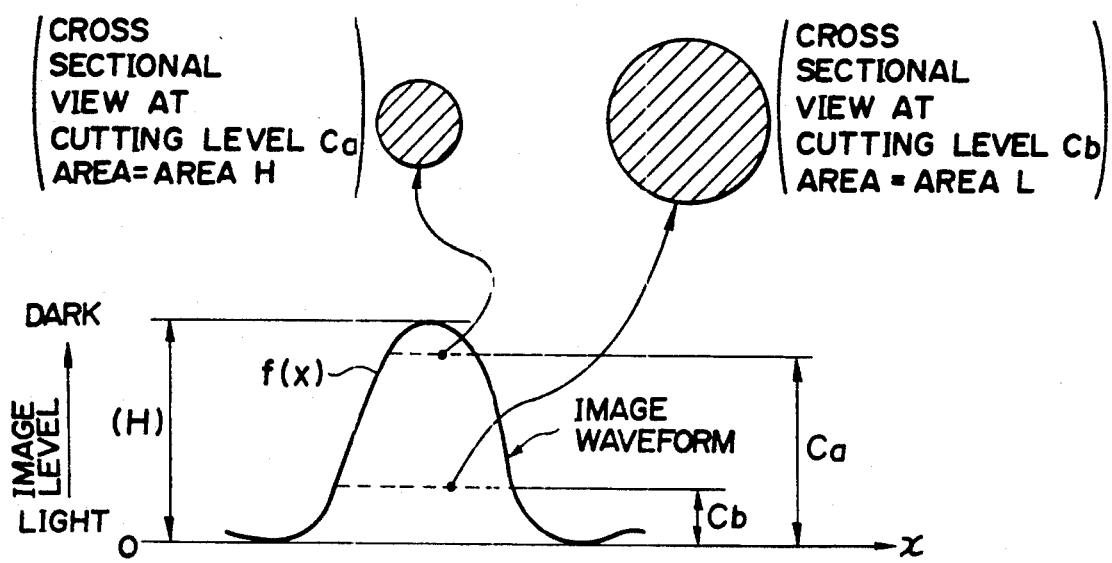
FIG. 2 is an explanatory diagram showing a part of the operation of the data processing means in FIG. 1.

The CCD line sensor 101 is driven by a sensor scan driving circuit 112, as controlled by a second control circuit 2A, and is made operative and can sequentially convert the image of a particle aggregation pattern on the microplate 100 into image line data in a state in which the aggregation pattern is cut by micro distances. The microplate 100 is sequentially moved to a plurality of very closely spaced positions. The CCD line sensor 101 obtains a set of image line data for each position of the microplate 100. Each set of image line data defines an image waveform or curve as illustrated in FIGS. 2 and 4. Each of these curves represents a generally one-dimensional component of the two-dimensional aggregation pattern image. The x-axis represents the scanning direction of the CCD line sensor Further, the embodiment shown in FIG. 1 comprises: a data memory circuit 3 to sequentially store a plurality of line data for one aggregation pattern which are output from the CCD line sensor 101 at predetermined timings; data processing means 4 to extract predetermined characteristic values to discriminate whether the aggregation pattern is positive or not on the basis of the data stored in the data memory circuit 3; a discriminating circuit 6 to discriminate whether the aggregation pattern is positive or not on the basis of the characteristic values which are output from the data processing means 4; and recording display means 7.

The data processing means 4 comprises: a cutting level output circuit 21 to output two high and low cutting levels in correspondence to the maximum value in the line data of the aggregation pattern; an area difference calculating section 22 to obtain a difference between areas at two high and low positions of the aggregation pattern which are obtained on the basis of the two high and low cutting levels; a cutting level difference calculating circuit 23 to obtain a difference between the two high and low cutting levels; and an HA data calculating section 24 to calculate a ratio of the area difference to the cutting level difference. Outputs of the area difference calculating section 22 and the HA data calculating section 24 are sent to the discriminating circuit 6 as predetermined characteristic values to discriminate the positivity about the aggregation pattern mentioned above.

The cutting level output circuit 21 has a first cutting level output circuit section 21A to output the cutting level of a larger value and a second cutting level output circuit section 21B to output the cutting level of a smaller value. The first and second cutting level output circuits 21A and 21B have multiplication parameters HQ (for example, 80%) and LQ (for instance, 20%), respectively. A maximum image value H is extracted from the aggregation pattern data by a maximum value extraction circuit 200. Circuits 21A and 21B respectively multiply HQ and LQ by the maximum value H. The circuits 21A and 21B can output the results of the multiplication as a first cutting level (i.e. image level) $C_a$ and a second cutting level (i.e. image level) $C_b$, where $C_a = H \cdot HQ$ = first cutting level, and $C_b = H \cdot LQ$ = second cutting level.

The area difference calculating section 22 has a first area calculating circuit 22A to calculate an area (area H) located at a height of 80% of the maximum value H of the aggregation pattern on the basis of the first cutting level $C_a$, and a second area calculating circuit 22B to calculate an area (area L) located at a height of 20% of the maximum value H of the aggregation pattern on the basis of the second cutting level $C_b$. FIG. 2 shows the relation between area H and area L. Further, the area difference calculating section 22 has an area difference calculating circuit 22C for calculating an absolute value SA of the difference between area H and area L. The absolute value SA (hereinafter referred to as an SA characteristic value), as output from circuit 22C, is one of the characteristic values.

On the other hand, the HA data calculating section 24 executes the following calculation as mentioned above:

$$HA = |\text{area H} - \text{area L}| / |C_a - C_b|.$$

Output HA data (hereinafter referred to as an HA characteristic value) of the HA data calculating section 24 is sent to the discriminating circuit 6 as another characteristic value to discriminate the positivity regarding the aggregation pattern data mentioned above.

Figure 3:
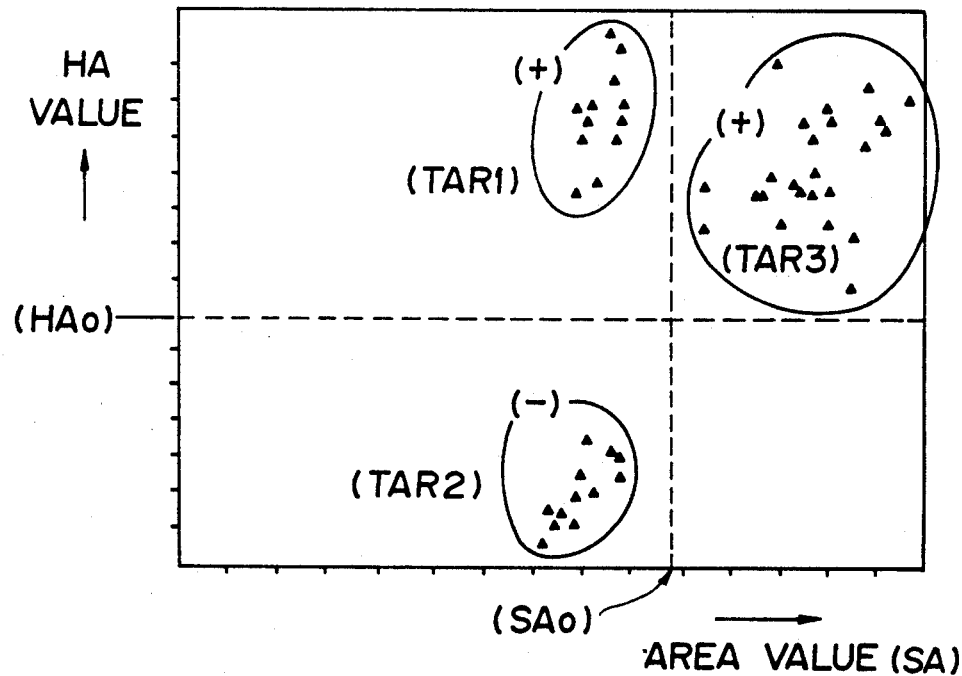
FIG. 3 is an explanatory diagram showing areas which are used in the discrimination by a discriminating circuit in FIG. 1.

The discriminating circuit 6 receives the outputs SA and HA respectively from the area difference calculating section 22 and the HA data calculating section 24 as characteristic values, thereby discriminating whether an object to be measured is positive or not on the basis of the aggregation pattern. A reference value setting circuit 5 is also provided for the discriminating circuit 6. The reference value setting circuit 5 outputs discrimination reference values $SA_0$ and $HA_0$ to discriminate whether the aggregation pattern being measured is positive or not based on the relationship of the outputs SA and HA to the reference values $SA_0$ and $HA_0$. The values of $SA_0$ and $HA_0$ are preset by the operator. FIG. 3 shows an example of experimental results of the analysis.

Figure 4A:
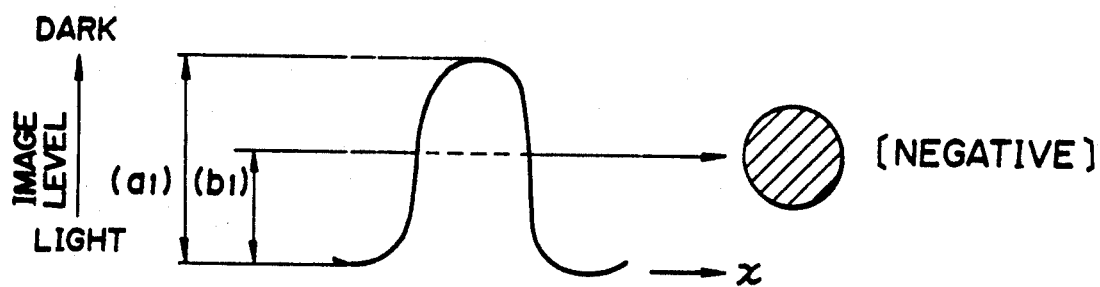
FIGS. 4(a), 4(b) and 4(c) are explanatory diagrams showing external portions of cross-sectional areas including the maximum value of an aggregation pattern and showing examples of positive and negative waveforms.
Figure 4B:
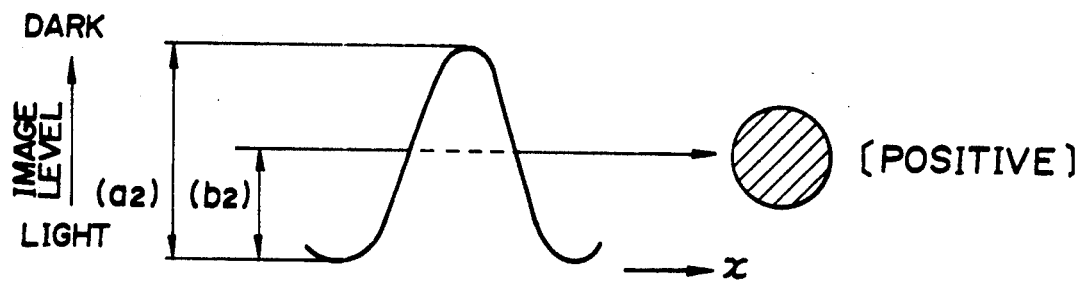
Figure 4C:
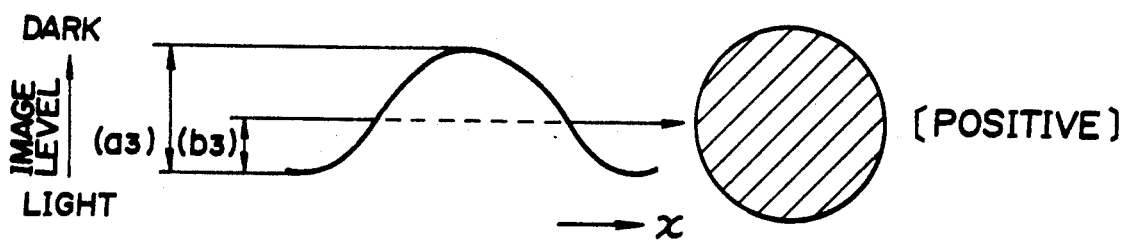

In the experiment result shown in FIG. 3, it is concluded that the waveforms in regions $TAR_1$ and $TAR_3$ are positive and waveforms in an area $TAR_2$ are negative. Explaining further in detail with reference to FIG. 4, as typical waveforms of the diagrams as vertical sectional views including the maximum value of the aggregation pattern, the waveforms of FIGS. 4(a)-4(c) are obvious from visual examination. In this case, in the conventional discrimination by the magnitude of the area, the position of the cutting level $b_1(\%) = b_2(\%) = b_3(\%)$ is first set. Since an obvious extent (i.e. large area) is seen at the cutting level $b_3$ in FIG. 4(c), it is determined to be a positive waveform. On the other hand, since there is no large extent (i.e. no large area) at cutting levels $b_1$ and $b_2$ in FIGS. 4(a) and 4(b), those two waveforms are determined to be negative using the conventional technique.

However, when considering from the waveform observation, the waveform of FIG. 4(b) is a typical positive pattern A contradictory point of the conventional technique occurs here.

On the other hand, according to the present invention, the cutting levels $C_a$ and $C_b$ are set by the method of FIG. 2 mentioned above and the HA characteristic values for FIGS. 4(a)-4(c) are calculated. Thus, the waveform of FIG. 4(a) is located in $TAR_2$ in FIG. 3, the waveform of FIG. 4(b) is located in TAR$_1$ in FIG. 3, and the waveform of FIG. 4(c) is located in TAR$_3$ in FIG. 3. Therefore, it will be obviously understood that the aggregation pattern having an HA characteristic value larger than the reference value HA$_0$ is positive. Thus, the drawback in the conventional area method can be eliminated and all of the discriminating processes can be automated without executing a judgment by the eyes.

The particular image pattern formed by the aggregation method depends on the degree to which the substance to be measured is inclined in the relevant specimen. Three patterns will now be considered in the following order: A negative specimen, a weak positive specimen, and a strong positive specimen.

Figure 5A:
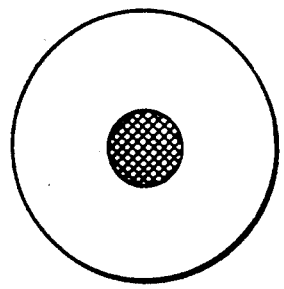
FIGS. 5(a) and 5(b) are explanatory diagrams showing examples of positive and negative aggregation patterns themselves.

(1) In the case of a negative specimen (FIG. 4a), the image pattern obtained is a circular image at the center having a clear outline, as depicted in FIG. 5a.

(2). In the case of a weak positive specimen (FIG. 4b), the image pattern obtained is a circular image similar to the negative image, but the outline is blurred.

Figure 5B:
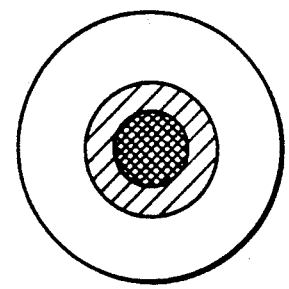

(3). In the case of a strong positive specimen (FIG. 4c), the image pattern obtained is a larger circle than that obtained for the negative specimen, and the outline is more blurred, as depicted in FIG. 5b. The density of the central portion is also obviously lower.

Among these three patterns, the patterns (1) and (3) for negative and strong positive specimens can be sufficiently distinguished by the size of the image at a certain density. However, in the case of a pattern (2) for a weak positive specimen, it is difficult to distinguish the image pattern from that for a negative specimen by merely comparing their sizes and, when the judgment is performed in the conventional visual manner, there are many cases where different individuals will reach different conclusions because of various factors (such as differences between individuals).

The usefulness of the HA characteristic value according to the present invention is evident from FIG. 3, which emphasizes that the HA characteristic value (along the vertical axis) for a weak positive specimen (TAR1) is significantly different from that for a negative specimen (TAR2). Therefore, use of the HA characteristic value according to the invention results in much more accurate differentiation between negative and weak positive specimens than is possible when using the conventional technique of visually estimating the degree of blur.

Other examples of criteria for discriminating positive aggregation patterns include: (1) SA>SA$_0$; or (2) SA>SA$_0$ and HA>HA$_0$. Using the disclosed invention, it is possible to provide an excellent method and apparatus for discriminating an aggregation pattern which cannot be obtained by the conventional method and in which the discrimination regarding the positivity of the aggregation pattern can be automatically performed. Therefore, a large number of discriminating operations can be promptly executed, and even with respect to an aggregation pattern of a small diffusion which has conventionally been decided to be negative by the area method, the positivity can be easily discriminated, so that the reliability of the whole apparatus can be remarkably increased.

It should be evident from the foregoing that the main control section 1 and data processing means 4 can be implemented using a conventional microprocessor circuit.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An apparatus for discriminating an aggregation pattern, comprising:

a light source which directs light onto a selected pattern to generate an optical image of said selected pattern;

a CCD line sensor;

means for effecting movement of said CCD line sensor relative to said optical image, said CCD line sensor outputting image line data at predetermined points in time during said relative movement;

a data memory circuit which is coupled to said CCD line sensor and sequentially stores said image line data output by said CCD line sensor at said predetermined points in time;

data processing means cooperable with said data memory circuit for determining first and second characteristic values based on said image line data; and discriminating means for discriminating whether or not said selected pattern is an aggregation pattern on the basis of said first and second characteristic values which are output from said data processing means;

wherein said data processing means includes maximum value extraction means responsive to said data memory circuit for determining a maximum image value of said image line data therein, image level output means responsive to said maximum value extraction means for outputting a high image level which is a value less than said maximum image value and a low image level which is a value less than said high image level, area determining means responsive to said data memory circuit and said image level output means for determining from said image line data in said data memory circuit first and second areas of said selected pattern which include only image values at least as large as said high image level and said low image level, respectively, whereby said first area is a portion of said second area; area difference calculating means responsive to said area determining means for outputting an area difference between said first and second areas, level difference calculating means responsive to said image level output means for outputting a level difference between said high and low image levels, data calculating means responsive to said area difference calculating means and said level difference calculating means for outputting a ratio of said area difference to said level difference, and means for respectively selecting said outputs of said area difference calculating means and said data calculating means to be said first and second characteristic values supplied to said discriminating means.

2. An apparatus according to claim 1, wherein said light source and said CCD line sensor are disposed on opposite sides of said selected pattern, and wherein said movement of said CCD line sensor relative to said optical image is rectilinear movement in a direction substantially perpendicular to the direction in which said line sensor extends, wherein said image line data taken at said predetermined points in time collectively represent a plurality of scan lines which are spaced from each other and parallel to each other.

3. An apparatus according to claim 1, wherein said discriminating means includes means for comparing said first and second characteristic values with respective first and second predetermined reference values, said discriminating means determining that said selected pattern is an aggregation pattern when one of said first and second characteristic values is found to be greater than a respective one of said first and second predetermined reference values.

4. An apparatus according to claim 1, wherein said discriminating means includes means for comparing said first and second characteristic values with respective first and second predetermined reference values, said discriminating means determining that said selected pattern is an aggregation pattern when said first characteristic value is greater than said first predetermined reference value and said second characteristic value is greater than said second predetermined reference value.

5. An apparatus according to claim 1, wherein said image level output means sets said high image level to a value which is approximately 80% of said maximum image value and sets said low image level to a value which is approximately 20% of said maximum image value.

* * * * *